United States Patent [19]

Takemura et al.

[11] Patent Number: 5,227,358
[45] Date of Patent: Jul. 13, 1993

[54] COMPOSITION HAVING STRONG AIR CLEANING ABILITY AND METHOD OF PREPARING SAME

[75] Inventors: Yozo Takemura, Tokyo; Tamio Noda, Tokai, both of Japan

[73] Assignee: Nippon Steel Corporation, Tokyo, Japan

[21] Appl. No.: 768,303

[22] PCT Filed: Feb. 8, 1991

[86] PCT No.: PCT/JP91/00155
  § 371 Date: Oct. 7, 1991
  § 102(e) Date: Oct. 7, 1991

[87] PCT Pub. No.: WO91/12076
  PCT Pub. Date: Aug. 22, 1991

[30] Foreign Application Priority Data

Feb. 10, 1990 [JP] Japan .................. 2-030431
Dec. 25, 1990 [JP] Japan .................. 2-406147

[51] Int. Cl.⁵ .............................................. B01J 23/00
[52] U.S. Cl. ................................. 502/316; 502/300; 502/305; 502/324; 502/325; 502/340; 502/345; 502/406; 502/414
[58] Field of Search .............. 502/300, 305, 316, 324, 502/325, 340, 345, 406, 414

[56] References Cited

U.S. PATENT DOCUMENTS 3,578,508  4/1967  Pearlman .................. 106/14.14

FOREIGN PATENT DOCUMENTS 156924  10/1985  European Pat. Off. .
62-101250  5/1987  Japan .
62-101251  5/1987  Japan .

OTHER PUBLICATIONS

World Patents Index Latest, JP-A-1272868 (1989).
World Patents Index Latest, JP-A-1266275 (1989).
World Patents Index Latest, JP-A-3188939 (1989).
World Patents Index, JP-A-54008725 (1979).

*Primary Examiner*—Patrick P. Garvin
*Assistant Examiner*—Brent M. Peebles
*Attorney, Agent, or Firm*—Wenderoth, Lind & Ponack

[57] ABSTRACT

A composition having a strong air cleaning ability, comprising co-existent products comprised of a reaction product of at least one metal selected from Fe, Mn, Cr, Ni, Zn, Al and Cu and alloys containing these metal elements with tannic acid and/or gallic acid or a reaction product with at least one acid or ascorbic acid, citric acid, tartaric acid and gluconic acid containing tannic acid and/or gallic acid, and an unreacted metal as mentioned above co-existing with the reaction product, and in some cases, further containing a co-existent product comprising iron hydroxide and/or a sulfide, and a method of preparing same.

11 Claims, No Drawings

COMPOSITION HAVING STRONG AIR CLEANING ABILITY AND METHOD OF PREPARING SAME

DESCRIPTION

1. Technical Field

The present invention relates to a composition having a strong air cleaning ability which can be used as an air cleaning material for cleaning polluted air containing toxic gases such as nitrogen oxides ($NC_x$), sulfur oxides ($SO_x$), and ozone ($O_3$) gas; nitrogen compound type gases such as ammonia ($NH_3$); sulfur compound type gases such as hydrogen sulfide ($H_2S$); carboxyl group type gases such as acetaldehyde; and carboxylic acid type gases such as acetic acid; or as a material for cleaning the air of combusted discharge gases or toxic gases, and a method of preparing same. The composition of the present invention also can be used as a food freshness retaining agent.

2. Background Art

The content of $NO_x$ gases, $SO_x$ gases and $O_3$ gas in the air must be reduced because they are a cause of aspiratory organ diseases, and various fuel devices, gas cleaning devices, and chemical treatment devices are used to prevent generation thereof, or to reduce the concentration thereof, in the air. Nevertheless, a method of efficiently removing these toxic gases from polluted air, by using simple equipment, has not been generally realized.

Nitrogen compound type gases or sulfur compound type gases in the air, which are a cause of objectionable odors, have been treated to remove these objectionable odors by the adsorption method using activated charcoal, the masking method using other fragrances, and the chemical method of carrying out a chemical reaction of odorous gases.

These deodorants of the prior art, however, have a problem in that the deodorizing ability thereof is soon lost.

The present inventors previously considered that the product of a reaction of a metal with a polybasic acid has a strong air cleaning effect, and filed an application for this invention under Japanese Patent Application No. 1-280776.

DISCLOSURE OF THE INVENTION

The object of the present invention is to provide a new air cleaning composition by which harmful $NO_x$ gases, $SO_x$ gases and $O_3$ gas are removed, to thereby clean the air, and at the same time, carboxyl group type gases, carboxylic acid type gases, nitrogen compound type gases, and sulfur compound type gases are removed.

Another object of the present invention is to provide a new air cleaning composition having a strong absorption ability which is able to remove toxic gases contained in gases discharged from internal combustion engines, objectionable odors, and toxic gases generated by chemical plants. In the present specification, the capability of removing such toxic gases and objectionable gases is called a strong air cleaning ability.

A further object of the present invention is to provide an air cleaning composition which can exhibit a strong air cleaning ability even when used over a long term.

In accordance with the present invention, there is provided a composition having a strong air cleaning ability and comprising, a product of a reaction of at least one metal selected from Fe, Mn, Cr, Ni, Zn, Al and Cu and alloys containing these metal elements with tannic acid and/or gallic acid, and a co-existent material consisting of an unreacted metal as mentioned above coexisting in the reaction product.

In accordance with the present invention, there is further provided a composition having a strong air cleaning ability and comprising, a product of a reaction of at least one metal selected from Fe, Mn, Cr, Ni, Zn, Al and Cu and alloys containing these metal elements with at least one acid selected from ascorbic acid, citric acid, tartaric acid and gluconic acid containing tannic acid and/or gallic acid, and a co-existent material consisting of an unreacted metal as mentioned above coexisting with the reaction product, and further, a coexistent material consisting of iron hydroxide and/or a sulfide.

BRIEF DESCRIPTION OF THE DRAWINGS

FIG. 1 is an illustration of the closed type deodorizing test vessel used in Example 2.

BEST MODE OF CARRYING OUT THE INVENTION

The present inventors found that, when a metal selected from Fe, Mn, Cr, Ni, Zn, Al and Cu or a powdery mixture of two or more of these metals or an alloy comprising two or more of these metals (hereinafter abbreviated as "metal such as iron, etc.") is allowed to react with tannic acid, and then dried in the air, the reaction product of the metal and tannic acid exhibits a strong air cleaning ability through a reaction with sulfur type compounds, nitrogen type compounds and lower fatty acids, toxic gases, and objectionable odor gases such as $SO_x$, $NO_x$, $O_3$, $CO_2$, CO, in the presence of oxygen and moisture in the air. The inventors also found that, although the reaction product undergoes a chemical change during the air cleaning process, when the metal is used in an excess amount, to thereby permit unreacted metal to remain and co-exist with the reaction product, the reaction product undergoes a chemical change (i.e., the reaction product is aged) and further, reacts with oxygen and moisture in the air, whereby a reaction product with a strong air cleaning ability is reproduced, to thus give an air cleaning material having a strong cleaning ability even when used over a long term.

Also, it has been found that gallic acid exhibits the same effect as that of tannic acid described above.

Regarding the manner in which the metal and the reaction product are permitted to co-exist, even when the reaction mixture in which the metal is allowed to react with tannic acid is added to or brought into contact with another metal, the same effect can be obtained.

Japanese Patent Application No. 1-280776, as mentioned above, discloses an air cleaning material using at least one acid selected from ascorbic acid, citric acid, tartaric acid, and gluconic acid. In this air cleaning material, the co-presence of a base is preferable for deodorizing, for example, hydrogen sulfide gas.

Nevertheless, the reaction product according to the present invention, using tannic acid or gallic acid, or an acid comprising a mixture thereof, can deodorize, for example, hydrogen sulfide gas, even when a base is not permitted to co-exist in the system.

Further, by using a mixed acid containing tannic acid and/or gallic acid in ascorbic acid, citric acid, tartaric acid and/or gluconic acid, when these acids are allowed to react with the above metal, a strong air cleaning ability will be exhibited for a wide range of toxic gases or objectionable odor gases, including hydrogen sulfide gas, even when a base is not permitted to exist, as in the case of using tannic acid and gallic acid or an acid comprising a mixture thereof. Also, in this case, when the metal is used in an excessive amount, to thereby permit the reaction product and the metal to co-exist, an air cleaning material having a strong air cleaning ability even when used over a long term can be obtained.

As described above, the reaction product of the present invention obtained by using a mixture of acids, can be stably obtained even without a mixing of the acids, by first allowing at least one acid selected from ascorbic acid, citric acid, tartaric acid and gluconic acid to react with a metal, to thus once form the reaction product in the air, and then dipping the product in tannic acid or gallic acid followed by drying, or by blowing the acid against the product followed by drying.

The present inventors assume that tannic acid or gallic acid has the action as described below, in the composition of the present invention having a strong air cleaning ability.

In the present invention, at least one acid selected from ascorbic acid, citric acid, tartaric acid and gluconic acid containing tannic acid and/or gallic acid (these acids are abbreviated hereinafter as tannic acid, etc.) is used.

As described below, the composition of the present invention having a strong air cleaning ability can be prepared by bringing a metal such as iron, etc. into contact with tannic acid, etc., followed by drying Due to this contact therebetween, the surface or crystal grain boundary of the iron, etc., is corroded by tannic acid, etc., or suffers a grain boundary corrosion, to thereby cause a fine unevenness thereof, whereby the surface area thereof is enlarged. Further, with an elapse of time, the reaction will proceed to thereby increase the number of cracks, whereby the surface area is further increased. The corroded surface is covered with a reaction product of a metal such as iron, etc., and tannic acid (which may be assumed to be a chain with a [OH] coordination bonded to $Fe^{2+}$ in complex). The structure of the reaction product is considered to be as follows.

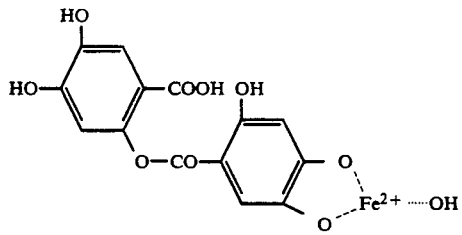

The composition according to the present invention has a broad contact area between a metal such as iron, etc., and the reaction product, and therefore, the chemical reaction between the metal such as iron, etc., and the reaction product will proceed smoothly, as described below. Further, since the reaction product is inserted to the grain boundary to thereby exhibit an anchoring effect therewith, the reaction product will not be detached but will be strongly adhered to a metal such as iron, etc., whereby a reproduction effect can be exhibited. This effect will be further improved if a metal such as iron, etc., is washed with an acid such as HCl or $H_2SO_4$ before contact thereof with a tannic acid, etc, or is brought into contact with tannic acid containing some HCl or $H_2SO_4$ added thereto.

The present inventors assume that the air cleaning mechanism of the present invention is as follows.

(i) Nitrogen compound type gas (e.g., $NH_3$) is primarily coordination-bonded to metal ions $M^{n+}$ in the reaction product, on the metal surface of the iron, etc., to thereby form an ammine complex.

Reaction product $+ NH_3 \rightarrow M^{n+}(NH_3)_m$ (ii) Since metals such as active iron, etc., immediately below the reaction product act as the catalyst, the $NH_3$ adsorbed on the metal surface reacts with a part of OH ions in the complex, and $O_2$ in the air reacts with $NH_3$ in the amine complex, as follows, to thereby partially reproduce the reaction product.

$O_2 + NH_3 \rightarrow N_2 + H_2O$ (iii) Metals such as active iron, etc., act as a reducing agent in the presence of oxygen and moisture in the air, whereby the following redox cyclic mechanism of tannic acid, etc., as shown below, is valid.

Aged tannic acid etc., + Metal reduction →
Reproduced tannic acid, etc.

(iv) Reproduced tannic acid, etc., reacts with oxidizing agents such as $NO_x$, $SO_x$, and $O_3$ to decompose harmful gases while forming new reaction products, to thereby form active oxygen.

Reproduced tannic acid + (oxidizing agent, moisture) → New reaction Product + S, N, + Active oxygen (v) Carboxyl group type gas (e.g., acetaldehyde), $NH_3$ and $H_2S$ are decomposed by an oxidation with active oxygen.

O + R—CHO, $NH_3$, $H_2S \rightarrow$ R—COOH (acetic acid), $N_2$, S, $H_2O$ (vi) Acetic acid or other lower fatty acids formed in the above reaction are fixed.

(vii) A part of $H_2S$ is precipitated by decomposition by the catalytic reaction with iron oxide, etc., as follows.

$H_2S \rightarrow HS + S$, $HS \rightarrow H + S$

In the present invention, as long as a metal such as iron, etc., exists, the reproduction mechanism works and tannic acid, etc. will continue to cause a corrosion reaction toward the center of the metal while maintaining the cleaning effect, whereby microscopic corrosion cracks of the metal are propagated to increase the surface area of the reaction product, and the air cleaning effect will continue over a long term.

The co-existent material according to the present invention having a strong air cleaning ability preferably has a ratio of tannic acid, etc., of 0.005 to 0.5 mol relative to 1 gram atom of the metal such as iron, etc. If the ratio of tannic acid, etc. is less than 0.005 mol per 1 gram atom of the metal such as iron, etc., the amount of reaction product produced may be insufficient. On the other hand, if tannic acid etc. is used at a ratio in excess of 0.5 mol, due to the presence of an excess amount of tannic acid, etc., the metal such as iron, etc. and the reaction product will become embedded with tannic acid, etc., i.e., the surface of the metal such as iron, etc., and the reaction product will be covered with tannic acid, etc., whereby the air cleaning ability will be weakened.

Since the tannic acid to be used in the present invention is naturally obtained, a tannic acid having a distinct molecular weight and a tannic acid having an indistinct molecular weight exist. If the tannic acid having an indistinct molecular weight is used, the desired effect can be substantially obtained if the concentration is calculated by using an estimated molecular weight of 350.

The tannic acid to be used in the present invention is also contained in Kraft black liquor or S·P waste liquor used in the paper making industry, and therefore, the acid obtained by using Kraft black liquor or S·P waste liquor is also included in the "tannic acid" to be used in the present invention.

The metal such as iron, etc., to be used in the present invention need not have a high purity, and metals containing usual impurities, for example, iron,, steel and ferromanganese, can be used, and further, the use of, for example, scraps or powder of metal recovered from metal production lines, such as iron, etc., enables a sufficient effect to be exhibited.

The metal such as iron, etc., to be used in the present invention includes metals such as iron, etc., produced by a plastic working such as rolling, extrusion, and drawing, as exemplified by steel plate, steel wire, steel pipe and foil, and a composition having a strong air cleaning ability can be prepared by using these materials. Also, the use of secondarily worked products obtained by subjecting molded products produced by plastic working to a secondary working, such as net products, honeycomb products, fiber products, and fine strip products, enables compositions having a strong air cleaning ability to be prepared. These compositions having a strong air cleaning ability and prepared by, for example, coating a metal such as iron, etc., with tannic acid, etc., can be used as an air cooling element without a special molding thereof.

According to the present invention, a composition having a strong air cleaning ability can be prepared by using a powder of a metal such as iron, etc. Namely, a desired composition can be obtained by dipping a powder of a metal such as iron, etc. in a solution of tannic acid, etc., and then taking out and drying the powder. Since the composition is powdery, by mixing a binder, for example, latex, with the powder before molding, a molded product having a strong cleaning ability and comprising a powdery composition can be obtained, and further, such a molded product is included in the air cleaning composition of the present invention. Also, a binder such as latex may be premixed with a powder of a metal such as iron, etc. before molding, and thereafter, the molded product coated with tannic acid, etc., followed by drying, whereby a molded product having a strong air cleaning ability is obtained, and such a molded product is also included in the present invention. The molded product obtained from a powder, in addition to those mentioned above, can be also obtained by, for example, coating the surface of a non-metal carrier with the powder and using latex, and the molded product of the powder molded by using a binder of the present invention also includes a molded product using these known powders. The compositions obtained by using these powders of metals such as iron, etc. or molded products thereof are preferable as they have a large surface area, and thus a large amount of reaction products can be permitted to coexist.

According to the present invention, the composition having a strong air cleaning ability can be prepared by using a non-metal or metal carrier having a metal such as iron, etc., flame sprayed or plated thereon. As the nonmetal carrier, for example, ceramics or organic porous materials such as urethane foam can be used. As the metal carrier, either a carrier of a metal such as iron, etc., or a metal carrier of a material different from iron, etc. may be employed. In this case, the flame sprayed or plated metal such as iron, etc., is permitted to act as the metal such as iron, etc., and thus the composition having a strong air cleaning ability has specific features of, for example, a light weight or strong corrosion resistance.

Further, the composition according to the present invention can be prepared by using a metal such as iron, etc., obtained by sintering. The shape of the sintered product can be a plate, tube, granule, or bulk, and these sintered products can be easily obtained by molding a kneaded product of a metal such as iron, etc. with CMC, and sintering the kneaded molded product. Also, the sintered product of the present invention includes three-dimensionally porous sintered products obtained, for example, by coating the skeleton of a urethane foam with a kneaded product of iron, etc. and CMC, and sintering the coated product. The urethane foam disappears due to pyrolysis during the sintering, and the iron, etc., coated on the skeleton will be sintered to give a three-dimensional porous sintered product. The composition having a strong air cleaning ability due to the use of a sintered product can be used, for example, as a deodorizing element. Also, the composition obtained by using a three-dimensional porous sintered product has three-dimensional communicating pores, and the reaction product is arranged on the surface of the communicating pores, and thus can be used as, for example, an air cleaning filter, without a special molding thereof.

Further, the composition according to the present invention can be prepared by the use of iron, etc., of a sintered product with a porosity of 15% or more. When the texture of the sintered product has many microvoids or macrovoids, the surface area therof becomes larger and a large amount of reaction products can be formed thereon. By mixing a powder of a metal such as iron, etc., with, for example, a powder of plastic scraps, kneading the mixture with CMC, molding the kneaded mixture and then sintering same, the powder or the plastic scraps will be eliminated by pyrolysis during the sintering, and all traces thereof will have disappeared after the pyrolysis, and therefore, the flow channels of the pyrolyzed gas will become microvoids or macrovoids, whereby a sintered product of a metal such as iron, etc., with a porosity of 15% or more can be prepared.

Further, according to the present invention, iron, etc., in the form of a powder, flakes, or fibers can be mixed and adhered with at least one fiber selected from synthetic fibers, glass fibers, natural fibers, cellulose, and carbon fibers, and formed into a nonwoven fabric, which can be used as the metal such as iron, etc., when preparing the composition. In this case, the metal such as iron, etc., in the form of a powder, flakes, or fibers may be, for example, first dipped in tannic acid, etc., and then taken out and dried, to form a co-existent product, which is, in turn, formed into a nonwoven fabric, or after a formation of the nonwoven fabric, the nonwoven fabric may be dipped in tannic acid, etc, and then taken out and dried, to form a co-existent product. Since a nonwoven fabric has an easily handleable shape, it is preferable for use, for example, as a sheet-shaped air cleaning element.

Furthermore, according to the present invention, the composition of the present invention can be prepared by permitting iron hydroxide and/or a sulfide to co-exist in various compositions having a strong air cleaning ability as described above.

According to experiments carried out by the present inventors, when a metal and iron hydroxide co-exist, a decomposition of $H_2S$ occurs due to a catalytic action, and when a metal and a sulfide co-exist, methylmercaptan is easily oxidized and decomposed by a catalytic action. Therefore, by permitting iron hydroxide and/or a sulfide to co-exist in the above-described various compositions having the basic deodorizing ability of the present invention, the ability thereof to remove $H_2S$ and methylmercaptan is improved.

Regarding the manner in which iron oxide is permitted to co-exist, this can be practiced by dipping a metal into a mixture containing an iron oxide-containing material obtained by mixing and reacting iron oxide or an alkali hydroxide such as $Ca(OH)_2$ or $NaOH$ with iron salts such as $FeSO_4$ or $FeCl_2$, mixed in tannic acid, etc.

Regarding the manner in which a sulfide is permitted to co-exist, for example, this can be practiced by dipping a metal carrier into a solution in which iron sulfide powder is added to a reaction mixture of tannic acid, etc., and a metal such as iron, etc. after the mixture has become approximately neutral. This can be also practiced by, for example, mixing iron sulfide powder and an organic solvent, etc., and blowing the mixture against a co-existent product of the reaction product of the metal and tannic acid, etc, and unreacted metal. As the sulfide, for example, in addition to the iron sulfide, manganese sulfide, sodium sulfide, copper sulfide, zinc sulfide, and silver sulfide may be effectively employed.

Also, a sulfide can be permitted to co-exist by bringing $H_2S$ gas into contact with the composition wherein the metal subjected to a reaction between a metal such as iron, etc., and tannic acid, etc., and the reaction product of the metal with tannic acid, etc., coexist.

Further, according to the present invention, when forming the reaction product, it is preferable to use an aqueous solution of tannic acid, etc., with a concentration of 0.01 to 5 mol. The metal such as iron, etc., may be dipped into the aqueous solution, and then taken out and dried to give a composition, or the aqueous solution can be blown against the metal such as iron, etc., and then dried to form a reaction product. According to the knowledge of the present inventors, if the concentration of the aqueous solution of tannic acid, etc., is less than 0.01 mol, the amount of reaction product is usually insufficient because the rate of formation of the reaction product is too slow, and in an aqueous solution with a concentration of more than 5 mol, a large amount of unreacted tannic acid, etc., remains, whereby the surface of the reaction product is covered with the acid, etc, and therefore, the strong air cleaning ability is lowered.

EXAMPLES

The present invention is now described in more detail with reference to Examples, which in no way limit the scope of the present invention.

EXAMPLE 1

Using the metals shown in Table 1, the compositions No. 1 to No. 4 of the present invention were prepared by the methods indicated in the preparation method column. The composition No. 5 in Table 1 is a Comparative example, and is a composition of pig iron powder, as described in Japanese Patent Application No. 1-280776, treated with ascorbic acid without the formulation of solid base. The composition No. 6 in Table 1 is a Comparative example and is a general purpose coconut hull activated charcoal.

First, 5 grams of the compositions No. 1 to No. 6 were charged into a vessel with an $NH_3$ concentration of 500 ppm, left to stand for 24 hours and the adsorbed amount of the $NH_3$ gas (% by weight) measured. The results are shown in Table 1, the first time adsorbed amount and $NH_3$ column. The samples of these compositions were left to stand in the air for 5 hours, and each sample left to stand in the air was again charged into a vessel with an $NH_3$ concentration of 500 ppm, left to stand for 24 hours, and the amount of $NH_3$ gas adsorbed was as shown in Table 1, the second time adsorbed amount and $NH_3$ column.

The first time adsorbed amount and $H_2S$ column in Table 1 shows the amount of $H_2S$ adsorbed when 5 grams of the compositions No. 1 to No. 6 were separately charged into a vessel with an $H_2S$ concentration of 500 ppm and left to stand for 24 hours. The second time adsorbed amount and $H_2S$ column shows the amount of $H_2S$ adsorbed when each sample used for the measurement of the first time adsorbed amount and $H_2S$ column was left to stand in the air for 5 hours, and then again charged into a vessel with an $H_2S$ concentration of 500 ppm and left to stand for 24 hours.

TABLE 1

| No. | Metal Kind | Metal Shape | Preparation Method | First time adsorbed amount $NH_3$ | First time adsorbed amount $H_2S$ | Second time adsorbed time $NH_3$ | Second time adsorbed time $H_2S$ |
|---|---|---|---|---|---|---|---|
| Example of Invention | | | | | | | |
| 1 | Pig iron | 50μ powder | Mixed in solution of pig iron: tannic acid = 1:0.1 and dried as such*2 | 3.1 | 1.5 | 3.0 | 1.5 |
| 2 | Fe–Mn | Sintered particles by use of 10μ powder | Dipped in tannic acid 0.5 mol solution and then dried*2 | 3.0 | 2.0 | 3.1 | 1.8 |
| 3 | Mn | *1 | Tannic acid 0.2 mol, gallic acid 0.5 mol solution blown and dried*2 | 2.8 | 2.5 | 2.8 | 2.5 |
| 4 | Al | 30μ powder | Mixed in tannic acid 0.05 mol, ascorbic acid 0.05 mol solution and | 3.0 | 1.3 | 3.1 | 1.5 |

TABLE 1-continued

| No. | Metal Kind | Shape | Preparation Method | First time adsorbed amount NH$_3$ | H$_2$S | Second time adsorbed time NH$_3$ | H$_2$S |
|---|---|---|---|---|---|---|---|
| | | | dried*2 | | | | |
| Comparative Example | | | | | | | |
| 5 | Pig iron | 50μ powder | Mixed and dried with ascorbic acid molar ratio 0.1*3 | 3.0 | 0.01 | 3.2 | 0 |
| 6 | Coconut full activated charcoal | 10μ powder | — | 0.06 | 0.25 | 0 | 0 |

*1Three-dimensional porous body obtained by coating urethane foam with kneaded product of 10μ powder and finder followed by sintering
*2Tannic acid is Tannic Acid AL, produced by Fuji Kagaku Kogyo K.K.
*3Ascorbic acid is L-ascorbic acid, produced by Takeda Yakuhin K.K.

As apparent from the results shown in Table 1, Compositions No. 1 to No. 4 of the present invention have a substantially equal air cleaning ability for NH$_3$ gas, but have a much stronger air cleaning ability for H$_2$S gas, compared with the No. 5 composition of the Comparative Example 1. Also, compositions Nos. 1 to 5 adsorbed amounts of NH$_3$ and H$_2$S gas were 5 to 50-fold compared with that adsorbed by composition No. 6. Namely, composition No. 6 had a second time adsorbed amount of 0 for both NH$_3$ gas and H$_2$S gas, and the gas adsorption ability thereof was not reproduced even when left to stand in the air. On the other hand, compositions Nos. 1 to 5 were able to reproduce the gas adsorption ability thereof when left to stand in the air, and in the second time adsorbed amount, exhibited an adsorbed gas amount substantially equal to the first time adsorbed amount.

EXAMPLE 2

Pig iron powder (average diameter 10 μm) was kneaded with CMC binder and water, added to urethane foam, and then sintered at 1150° C. to prepare an -iron porous body, followed by practicing the chemical solution treatment shown in Table 2.

When the above sample was tested in a 1 m$^3$ closed type deodorizing test vessel shown in FIG. 1, the concentration in the test vessel after 30 minutes was as shown in Table 3, wherein Samples B and C showed an improved methylmercaptan removal ratio, and C also showed an improved H$_2$S removal ratio. In FIG. 1, 1 is a gas inlet hole, 2 a gas discharge hole, 3 the iron porous body after the chemical solution treatment, and 4 a fan.

TABLE 2

| Iron porous body sample | Chemical solution treatment method |
|---|---|
| A | Dipped in (Tannic acid 0.2 M/l + Ascorbic acid 0.2 M/l) mixture for 3 min. and then dried |
| B | Mixture of (iron sulfide powder 50 g/ethylalcohol/liter) blown against Sample A |
| C | Dipped in (ascorbic acid 0.2 M/l + FeSO$_4$ 0.4 M/l + Ca(OH)$_2$ 0.5 M/l + iron sulfide powder 20 g/l) mixture for 3 min. and dried |
| D | Dipped in ascorbic acid 0.2 M/l for 3 min and dried, then dipped in tannic acid 0.1 M/l for 30 min. and dried |

TABLE 3

| Sample | Conc. (ppm) NH$_3$ Initial stage | NH$_3$ After 30 min. | H$_2$S Initial stage | H$_2$S After 30 min. | CH$_3$HS Initial state | CH$_3$HS After 30 min. |
|---|---|---|---|---|---|---|
| A | 30 | 6 | 20 | 3 | 10 | 6 |
| B | 30 | 6 | 20 | 3 | 10 | 3 |
| C | 30 | 7 | 20 | 0 | 10 | 2 |
| D | 30 | 4 | 20 | 2 | 10 | 5 |

UTILIZABILITY IN INDUSTRY

An described above, the composition of the present invention having a strong air cleaning ability can remove harmful NO$_x$ gases, SO$_x$ gases, and O$_3$ gas, and further, can remove nitrogen compound type gases, sulfur compound type gases, and lower fatty acids, which are a cause of objectionable odors.

The composition of the present invention having a strong air cleaning ability exhibits this strong air cleaning ability even when used over a long term. The composition of the present invention having a strong air cleaning ability, different from that described in Japanese Patent Application No. 1-280766, has a strong air cleaning ability for H$_2$S gas, even without the formulation of a solid base. According to the knowledge of the present inventors, the compositions of the present invention having a strong air cleaning ability also have a food freshness retaining ability.

We claim:

1. A composition having a strong air cleaning ability and comprising a reaction product of at least one metal selected from Fe, Mn, Cr, Ni, Zn, Al and Cu and alloys containing these metal elements with tannic acid and/or gallic acid, and an unreacted metal co-existing with said reaction product.

2. A composition having a strong air cleaning ability and comprising co-existent products comprised of a reaction product of at least one metal selected from Fe, Mn, Cr, Ni, Zn, Al and Cu and alloys containing these metal elements with at least one acid selected from ascorbic acid, citric acid, tartaric acid and gluconic acid, a reaction product of said at least one metal or alloy with tannic acid and/or gallic acid, and an unreacted metal co-existing with said reaction products.

3. A composition according to claim 1 or claim 2, wherein the co-existing products contain 0.005 to 0.5 mole of acid per 1 gram atom of metal.

4. A composition according to claim 1 or claim 2, wherein the metal is a molded product molded by plastic working or a secondary worked product of said molded product.

5. A composition according to claim 1 or claim 2, wherein the metal is metal powder or a molded product of metal powder molded by using a binder.

6. A composition according to claim 1 or claim 2, wherein the metal is a metal which is flame sprayed or plated on a non-metal or metal carrier.

7. A composition according to claim 1 or claim 2, wherein the metal is a plate-shaped, tubular, particulate, hollow, bulky or three-dimensional porous sintered product.

8. A composition according to claim 7, wherein the sintered product is a sintered product with a porosity of 15% or more obtained by using a pyrolytic material which generates gas during sintering.

9. A composition according to claim 1 or claim 2, wherein the metal is a powdery, flaky or fibrous metal forming a nonwoven fabric mixed and adhered with at least one member selected from synthetic fibers, glass fibers, natural fiber, cellulose and carbon fibers.

10. A composition according to claim 1 or claim 2, further comprising at least one of iron hydroxide and sulfides co-existent therewith.

11. A method of preparing a composition having a strong air cleaning ability according to claim 1 or claim 2, wherein a co-existence of the metal and the reaction product is effected by dipping the metal in an aqueous solution of the acid with a concentration of 0.01 to 5 mol and taking out the metal, or blowing said aqueous solution against the metal, followed by drying.

* * * * *